United States Patent [19]
Bramucci et al.

[11] Patent Number: 6,048,694
[45] Date of Patent: Apr. 11, 2000

[54] BACTERIAL POSITIVE SELECTION VECTOR

[75] Inventors: Michael Gene Bramucci, Milmont Park, Pa.; Vasantha Nagarajan, Wilmington, Del.

[73] Assignee: E. I. du Pont de Nemours and Company, Wilmington, Del.

[21] Appl. No.: 09/068,043

[22] PCT Filed: Oct. 31, 1996

[86] PCT No.: PCT/US96/17636

§ 371 Date: Apr. 30, 1998

§ 102(e) Date: Apr. 30, 1998

[87] PCT Pub. No.: WO97/16558

PCT Pub. Date: May 9, 1997

Related U.S. Application Data

[63] Continuation-in-part of application No. PCT/US96/00017, Oct. 31, 1996
[60] Provisional application No. 60/006,201, Nov. 3, 1995.

[51] Int. Cl.[7] .............................. C12Q 1/68; C12N 15/74; C12N 15/76; C12N 15/00; C12N 1/20
[52] U.S. Cl. .............................. 435/6; 435/471; 435/476; 435/479; 435/485; 435/486; 435/487; 435/320.1; 435/252.3; 435/252.31; 435/252.35
[58] Field of Search ..................................... 435/485, 486, 435/320.1, 252.31, 6, 471, 476, 479, 487, 252.3, 252.35

[56] References Cited

U.S. PATENT DOCUMENTS 5,162,207  11/1992  Nagarajan et al. ..................... 435/69.1

FOREIGN PATENT DOCUMENTS

WO 91/00913  1/1991  WIPO.

OTHER PUBLICATIONS

Sambrook et al., Molecular Cloning, a Laboratory Manual, Cold Spring Harbor Laboratory Press, Cold Spring Harbor, N.Y., 1.85–1.86, see also 1.56–1.58.
Cai et al., *J. Bacteriol.*, 172, 3138, 1990.
Gay et al., *J. Bacteriol.*, 164, 918, 1985.
Jager et al., *FEMS Microbiol. Let.*, 126, 1, 1995.
Jager et al., *J. Bacteriol.*, 174, 5462, 1992.
Kamoun et al., *Mol. Microbiol.*, 6, 809, 1992.
Kaniga et al., *Gene*, 109, 137, 1991.
Ried et al., *Gene*, 57, 239, 1987.
Simon et al., *J. Bacteriol.*, 173, 1502, 1991.
Gay et al., *J. Bacteriol.*, 153, 1424, 1983.
Lepesant et al., *Mol. Gen. Genet.*, 128, 213, 1974.
Pierce et al., *Proceed. Natl. Acad. Sci. USA*, 89, 2056, 1992.
Errington, *Microbiol Reviews*, 57, 1, 1993.
Bron S. et al., Molecular Biological Methods for Bacillus, C.R. Harwood and S.M. Cutting (eds.), John Wiley & Sons, New York, 75–174, 1990.
Nagarajan et al., *Res. Microbiol.*, 142, 787, 1991.
Yudkim, *Mol. Gen. Genet.*, 202, 55, 1986.
Ferrari et al., *Proc. Natl. Acad. Sci., USA*, 82, 2647, 1985.
Hasnain et al., *J. Gen. Microbiol.*, 132, 1863, 1986.
Young et al., Biotechnology Handbooks, N.P. Minton and D. J. Clarke (eds.), 3, Clostridia, Plenum Press, 63–103, 1989.
Schwartz et al., *Appl. Microbiol. Biotechnol.*, 27, 50, 1987.
Soutschek–Bauer et al., *Mol. Gen. Genet.*, 208, 537–541, 1987.
Garnier et al., *Plasmid*, 19, 134, 1988.
M.G. Bramucci et al., Applied and Environmental Microbiology, 62(11), 3948–3953, 1996.
T.V. Borchert et al., *J. Bacteriol.*, 173, 276–282, 1991.

*Primary Examiner*—Remy Yucel

[57] ABSTRACT

A positive selection vector is provided for the transformation and screening of Gram positive bacteria and particularly Bacillus sp. for the presence of foreign DNA. The vector comprises a mutant gene encoding a signal peptide processing mutation. Expression of the mutant gene in a Bacillus host cell which lacks the ability to metabolize sucrose is lethal when cells are grown in the presence of sucrose. Foreign DNA may be inserted into the vector so as to inactivate the mutant gene thereby permitting the cells to grow in the presence of sucrose and allowing for facile selection of transformants.

17 Claims, 4 Drawing Sheets

BACTERIAL POSITIVE SELECTION VECTOR

This application is a continuation of PCT/US96/00017, filed Oct. 31, 1996 which claims the benefit of U.S. Provisional Application No. 60/006,201, filed Nov. 3, 1995.

FIELD OF INVENTION

The present invention relates to the field of molecular biology and the use of selection vectors for the identification of recombinant bacteria containing heterologous DNA. More specifically a *B. amyloliquifaciens* signal sequence mutant gene has been discovered that conveys lethality to Bacillus sp. and may be used in a method for the direct selection of recombinant Bacillus host cells containing cloned, foreign DNA.

BACKGROUND

A method for readily isolating bacteria with cloned DNA is essential for successfully cloning DNA from any source. Identification of bacteria containing cloned DNA is most easily accomplished whenever the cloned DNA encodes a function that can be subjected to direct genetic selection, i.e., whenever survival of recombinant bacteria depends upon acquiring and expressing a function encoded by the DNA that is to be cloned. Identifying recombinant bacteria with cloned DNA is significantly more difficult when the cloned DNA does not encode a genetically selectable function because recombinant bacteria with cloned DNA must be identified against a potentially high background of recombinant bacteria that contain the cloning vector but lack DNA.

One approach to identifying recombinant bacteria with cloned inserts is to screen bacterial colonies for insertional inactivation of a reporter gene such as lacZ, the structural gene for β-galactosidase (Sambrook et al., Molecular Cloning, A Laboratory Manual, p. 1.85–p. 1.86 Cold Spring Harbor Laboratory Press, Cold Spring Harbor, N.Y.). β-galactosidase can not be made when DNA is cloned into a restriction site that separates the coding portion of lacZ from its promoter. As a result, on medium with the chromogenic substrate X-gal, recombinants with cloned DNA appear as white colonies against a background of blue recombinant colonies that contain religated vector alone. Screening methods such as insertional inactivation of lacZ facilitate identification of bacteria with cloned DNA by flagging the appropriate colonies in some way. However, these methods do not favor or select for growth of bacteria with cloned DNA. Hence, whenever a screening procedure is used, it is usually necessary to look through large numbers of colonies to find a few with cloned DNA. A common strategy for reducing the number of background colonies is to prevent self-ligation of the vectors by using alkaline phosphatase to remove the terminal 5' phosphates from vector molecules because DNA ligase requires a terminal 5' phosphate to join the ends of DNA molecules (Sambrook et al. supra, p. 1.56–p. 1.58). This method generally reduces, but does not eliminate, background colonies lacking cloned DNA.

An approach that minimizes the number of bacteria lacking cloned inserts uses a vector that enables direct selection for recombinant bacteria with cloned DNA. The advantage of a selection method over a screening method is that growth of bacteria with cloned DNA is greatly favored over bacteria lacking cloned DNA.

Direct or positive selection vectors containing genes that convey lethality to the host are well known. For example, expression of the *B. subtilis* or the *B. amyloliquefaciens* sacB genes in the presence of sucrose is lethal to *E. coli* and a variety of other Gram-negative and Gram-positive bacteria [Cai et al., *J. Bacteriol.* 172, 3138, (1990); Gay et al., *J. Bacteriol.* 164, 918, (1985); Jager et al., *FEMS Microbiol.* Let. 126,1 (1995); Jager et al., *J. Bacteriol.* 174, 5462, (1992); Kamoun et al., *Mol. Microbiol.* 6,809, (1992); Kaniga et al., *Gene* 109,137 (1991); Ried et al., *Gene* 57,239, (1987); Simon et al., *J. Bacteriol.* 173,1502, (1991)]. The sacB gene encodes levansucrase [Gay et al., *J. Bacteriol.* 153,1424 (1983); Lepesant et al., *Mol. Gen Genet.* 128,213 (1974)]. Levansucrase catalyzes both the hydrolysis of sucrose and the polymerization of sucrose to form levan. The basis for the lethality of levansucrase in the presence of sucrose is not fully understood. However, the inability of *E. coli* and certain other bacteria to grow if sacB is expressed in the presence of sucrose means that inactivation of sacB can be used to directly select for bacteria that contain DNA inserted into sacB (Cai and Wolk, ibid.; Gay et al., supra.; Jager et al., supra.; Kaniga et al., supra.; Ried et al.,, supra; Simon et al., supra.]. Indeed, insertional inactivation of the wild type *B. amyloliquefaciens* sacB gene has been used to select for cloned DNA in *E. coli* [Pierce et al., *Proceed. Natl. Acad. Sci. USA* 89,2056 (1992)].

*B. subtilis* is an important alternative to *E. coli* for cloning of DNA. *B. subtilis* does not have lipopolysaccharide as a cell well component and, as a result, does not contaminate extracellular products with endotoxin [Harwood et al., p. 327–390. In C. R. Harwood and S. M. Cutting (eds.), *Molecular Biological Methods for Bacillus* (1990) John Wiley & Sons, New York]. Proteins secreted from *B. subtilis* are released into the culture medium rather than being trapped in a periplasmic space as is frequently the case for *E. coli* and other Gram negative bacteria (Harwood et al., supra). In addition to use as a tool for biotechnology, *B. subtilis* is intensively studied as a model system for cellular differentiation because of its ability to sporulate [(Errington, *Microbiol. Reviews.* 57,1 (1993)). Many sporulation genes have no counterparts in *E. coli*. As a result, the function of many sporulation genes can be properly examined only in *B. subtilis.*

Although the systems for genetic manipulation of *B. subtilis* are nearly as well developed as for *E. coli*, utilization of *B. subtilis* has lagged behind use of *E. coli* for cloning purposes. One problem is that identifying recombinant bacteria with cloned inserts is significantly more difficult with *B. subtilis* than with *E. coli*. Nicked plasmids, useful for genetic manipulations in *E. coli*, are inactive in transformation of *B. subtilis* [Bron, S., p. 75–174. In C. R. Harwood and S. M. Cutting (eds.), *Molecular Biological Methods for Bacillus* (1990) John Wiley & Sons, New York]. Consequently, *B. subtilis* cannot be transformed with vector molecules that have been dephosphorylated by alkaline phosphatase and ligated. This is a strategy commonly employed with *E. coli* for enrichment of molecules with inserts but cannot be applied to *B. subtilis*. Furthermore, the wild-type alleles of sacB from *B. subtilis* or *B. amyloliquifaciens*, useful in *E. coli* because of their lethality, cannot be used to select for cloned DNA in *B. subtilis* because expression of these alleles is not lethal for *B. subtilis* [Nagarajan et al., *Res. Microbiol.* 142,787 (1991)].

In an attempt to overcome the difficulty of genetic manipulations in Bacillus a variety of shuttle vectors have been developed for *E. coli* and *B. subtilis* so that DNA can be initially cloned in *E. coli* and then transferred to *B. subtilis* for subsequent manipulation (Bron, supra). However, it is well known that functional copies of certain genes can be expressed in *B. subtilis* but not in *E. coli*. In some cases, expression of a heterologous gene is toxic for *E. coli*. [Yudkin, *Mol. Gen. Genet.* 202,55 (1986); Ferrari et al., *Proc. Natl. Acad. Sci. USA* 82,2647 (1985); Hasnain et al., *J. Gen Microbiol.* 132,1863 (1986)]. Young et al., [p. 63–p. 103. In N. P. Minton and D. J. Clarke (eds.), *Biotechnology Handbooks, Vol.* 3, *Clostridia* (1989) Plenum Press, New York.]. Furthermore, there are a number instances where *E. coli* may be unsuitable for production of proteins encoded by certain heterologus genes. For example it would appear that *B. subtilis* is a preferred host for production of clostridial enzymes because overproduction of the *Clostridium thermocellum* celA gene product is known to result in rapid loss of viability for *E. coli* but not for *B. subtilis* [Schwartz et al., *Appl. Microbiol. Biotechnol.* 27,50, (1987); Soutschek-Bauer et al., *Mol. Gen. Genet.* 208:537–541 (1987)]. In other cases, differences in preferred codon usage may allow a gene to be translated in *B. subtilis* but not in *E. coli* [Garnier et al., *Plasmid* 19,134, (1988)].

There is a need, therefore, for vectors and methods that can be used to efficiently isolate recombinant molecules containing cloned DNA in *B. subtilis* without recourse to *E. coli* based systems. The problem to be solved is to develop a means of directly transforming Bacillus with plasmid DNA in such a way that transformants with inserts in the plasmid are selected for growth and transformants without inserts in the plasmid are non-viable. Applicant has solved this problem through the development of a positive selection vector for Bacillus. The selection vector makes use of a mutant levansucrase gene that confers lethality on the host Bacillus cell in the presence of sucrose. Insertion of foreign DNA into a cloning site within the mutant levansucrase gene results in the inactivation of the gene and allows the cell to grow. All cells transformed with vector molecules that lack foreign DNA inserts will not grow. In this fashion the vector permits the selection of colonies that contain inserts, while at the same time limiting the number of cells containing non-productive vector that must be screened.

SUMMARY OF THE INVENTION

The present invention provides a method for the positive selection of Bacillus sp. hosts transformed with heterologus DNA comprising:

(i) constructing a positive selection vector comprising:
(a) a mutant gene encoding a signal peptide processing mutation, the gene additionally encoding a levansucrase polymerase activity and containing compatible restriction sites useful for the insertion of heterologous DNA;
(b) a gene encoding antibiotic resistance;
(c) a host specific origin of replication for maintaining the vector as multicopy; and
(d) suitable regulatory sequences for the regulation and expression of the mutant gene;
(ii) isolating the heterologous DNA;
(iii) cloning the isolated heterologous DNA into the compatible restriction sites of the mutant gene wherein the levansucrase polymerase activity is destroyed;
(iv) transforming a competent host cell with the vector of step (iii) wherein the host cell does not possess the ability to metabolize sucrose;
(v) incubating the transformed host cells in the presence of a suitable growth media containing sucrose; and
(vi) isolating transformants capable of growing in the presence of sucrose.

It is a further object of the present invention to provide a DNA fragment useful in a positive selection vector encoding a mutant levansucrase enzyme and having the nucleic acid sequence as defined in SEQ ID NO.:1.

DETAILED DESCRIPTION OF THE INVENTION

Figure 1A:
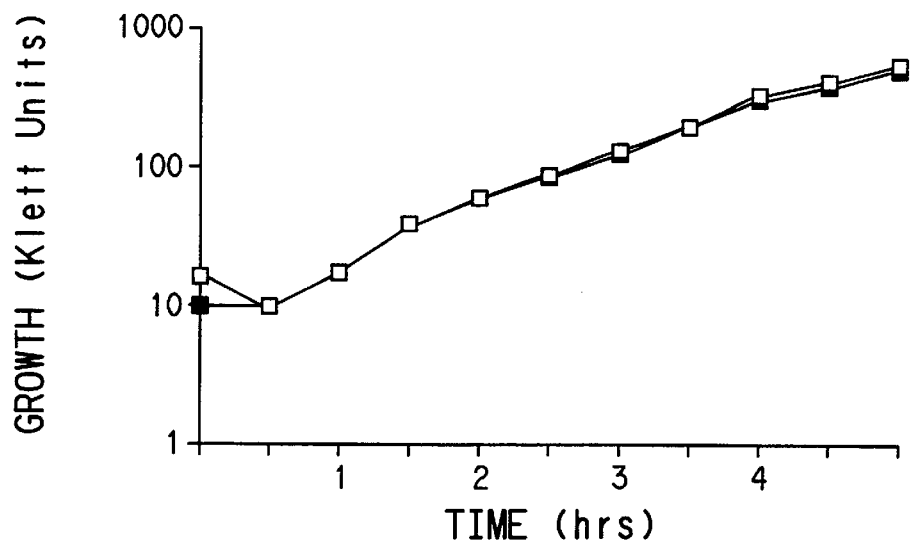
FIGS. 1A and 1B are graphic illustrations of the growth of BE1510(pBE504) and BE1510(pBE517) with and without sucrose.

As used herein the following terms may be used for interpretation of the claims and specification.

The term "foreign DNA" or "heterologus DNA" will mean DNA that is derived from a source other than the cell in which it is begin expressed The term "fragment" will refer to a fraction of the DNA sequence of the particular region.

As used herein, "transformation" is the acquisition of new genes in a cell by the incorporation of nucleic acid.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and the transcribed messenger RNA is then translated into the gene protein product.

As used herein the term "host cell" will refer to a cell that has been transformed with heterologus DNA. Host cells useful in the present invention are typically Bacillus which lack the ability to metabolize sucrose.

The term "plasmid" or "vector" as used herein refers to an extra-chromosomal element often carrying genes which are not part of the central metabolism of the cell, and usually in the form of circular double-stranded DNA molecules.

As use herein the term "positive selection vector" will refer to a vector that is useful for the transformation and selection of host cells with heterologus DNA. Positive selection vectors of the present invention will contain a gene whose expression is lethal to a host cell. Insertion of foreign or heterologus DNA at any point within that gene inactivates the lethal trait and allows the host cell to grow and be selected.

The term "sacB[BamP]W29" refers to a gene containing a mutation in the signal peptide of levansucrase and whose expression in a host cell is lethal under the appropriate conditions.

As used herein the term "insert" or "DNA insert" will refer to fragments of heterologus DNA that are inserted into a positive selection vector for the purpose of transforming a suitable host cell.

"Compatible restriction sites" refers to different restriction sites that, when cleaved, yield nucleotide ends that can be ligated without any additional modification.

"Shuttle vector" is a vector that is double stranded normally and contains both the origins of replication for *E. coli* and *B. subtilis* and also the F1 intragenic region for the preparation of single stranded DNA.

As used herein, the designation "ATCC" refers to the American Type Culture Collection depository located at 10801 University Blvd, Manassas, Va. 20110-2209 U.S.A. The "ATCC No." is the accession number to the following cultures on deposit under terms of the Budapest Treaty at the ATCC:

| Identification Reference | ATCC Designation | Deposit Date |
| --- | --- | --- |
| BE1510 (*B. Subtilis*) | 69947 | November 3, 1995 |
| BE1510 (pMGB161) (*B. Subtilis*) | 69946 | November 3, 1995 |
| BE1510 (pMGB161ΔCat1) (*B. Subtilis*) | 69945 | November 3, 1995 |

The invention provides a unique positive selection vector useful for the transformation and selection of Bacillus sp. with heterologus DNA. The selection vector makes use of a gene encoding a mutant levansucrase signal peptide that confers lethality on the host Bacillus cell in the presence of sucrose. Insertion of foreign DNA into a cloning site within the structural gene results in the inactivation of the gene and allows the cell to grow. All cells transformed with the vector but lacking the foreign DNA insertion will not grow. In this fashion the vector permits the selection of colonies that contain inserts, while at the same time limiting the number of cells containing a vector lacking inserts that must be screened out.

The present vector is the only positive selection vector known in the art for Bacillus. The vector is useful for cloning foreign DNA of any organism where expression of that DNA is compatible with Bacillus growth. The invention is particularly useful for the creation of genomic libraries in Bacillus or for the screening of clones containing specific intact structural genes.

Heterologus DNA:

It is contemplated that the present method will be useful for the cloning of a diverse spectrum of foreign DNA. Foreign DNA particularly useful in the present method include but are not limited to genes encoding: industrial enzymes from thermophiles and mesophiles such as: protease, esterase, pectinase, xylanase, amylase, cellulase, levanase, lipase, rnase, nucleotidase, transfructosylase, lactase, glucose isomerase phosphatase; biotin binding proteins such as avidin and streptavidin; immunoglobin binding proteins such as protein A, protein G and protein L; immunoglobins, receptor proteins, and structural proteins such as actin, fibrin, collagen, silk proteins and elastin; as well as viral proteins such as protease reverse transcriptase and envelope proteins; and antigens from microbes and protozoa such as staphylococcus protein A, levansucrase, and barnase.

Signal Peptidase Cleavage Site: sacB[BamP]W29

Signal peptidase cleavage can be inhibited when large amino acids are substituted at −1 or −3 position of the signal peptide. +1 refers to the N-terminal amino acid of the mature, secreted protein. −1 refers to C-terminal amino acid of the signal peptide. Cleavage normally occurs at the junction of −1 and +1.

The mutant *B. amyloliquifaciens* sacB[BamP]W29 gene was first reported by Borchert and Nagarajan, [*J. Bacteriol.* 173, 276, (1991)] where it was determined that the gene contained a mutation that interfered with the processing of the signal peptide associated with levansucrase. The sequence of the mutant gene is shown in SEQ ID NO.:1.

The W29 mutation changes alanine into tryptophan at the −1 position of the signal peptide encoded by the wild-type *B. amyloliquifaciens* levansucrase gene (sacB[BamP]). Expression of the w29 mutation in *B. subtilis* resulted in a 90% reduction of extracellular levansucrase as compared with wild-type activity.

Expression of the wild-type *B. amyloliquifaciens* sacB [BamP] gene does not inhibit growth of *B. subtilis* (Nagarajan et al., supra). Furthermore, *B. subtilis* strains with plasmids containing the W29 mutation have been previously cultured in synthetic liquid medium in the presence of sucrose for short periods of time to analyze processing of the levansucrase signal peptide (Borchert et al., supra). The W29 mutation was not observed to adversely affect the viability or growth of host bacteria under the conditions of these experiments. However, applicant has discovered *B. subtilis* transformed with the W29 mutation exhibits significant growth inhibition and even lethality when grown for extended periods in the presence of sucrose. By "extended periods" it is meant longer than 2 hours. The growth inhibition conveyed by the W29 mutation makes this gene an excellent candidate for incorporation into a positive selection vector for the transformation of Bacillus with heterologus DNA.

Signal peptide processing defect is not limited to sacB [BamP]W29 mutation and includes the following mutations. Substitutions of proline, glutamine, tyrosine, glutamic acid, aspartic acid and histidine at −1 position are expected to have an effect similar to that of sacB[BamP]W29. Substitutions at −3 also will have similar effect and thus substitution of tryptophan, proline, glutamine, tyrosine, glutamic acid, aspartic acid and histidine will result in a signal peptide processing defect. The present invention includes all signal peptide processing mutants and is not limited to levansucrase signal peptide. Other useful signal peptides are listed in Table 1 of Nagarajan. (Nagarajan, V. 1993 Protein secretion in *B. subtilis*. 713–729. Sonenshein, Hoch and Losick (Eds.). In *B. subtilis* and other Gram-positive bacteria Physiology, Biochemistry and Molecular Genetics ASM Washington D.C.)

It has been shown that amino acid substitutions in the wild-type levansucrase enzyme will destroy enzyme activity. Specifically, Chambert and Petit-Glatron (*Biochem. J.* 279,35, (1991)] have demonstrated that converting the arginine in position 331 of levansucrase ($Arg^{331}$) to leucine (Leu) inactivates the polymerase activity of the enzyme. Using similar methods, Applicant has modified the sacB [BamP]W29 gene so as to encode a protein containing a leucine in the 331 position which was used to transform competent Bacillus host cells. Where cells transformed with the unmodified W29 gene were unable to grow in the presence of sucrose, cells transformed with the gene expressing the leucine modified protein showed no growth inhibition with sucrose. The ability to reverse lethality of the W29 mutation by inactivating the polymerase activity indicates that the sacB[Bamp]W29 gene is clearly responsible for the lethal trait. Additionally, since inactivation of its polymerase activity reverses lethality it is contemplated that any disruption in the gene that interferes with the polymerase activity of the enzyme may be a useful tool in the design of positive selection vectors.

Host Cells:

The present invention provides host cells useful for the expression of foreign or heterologus DNA. The present method relies on a host cell whose growth is inhibited in the presence of the sacB[BamP]W29 gene containing a mutation for the processing of the levansucrase signal peptide. The growth inhibition or lethality in these cells is the result of metabolism of sucrose (Pierce et al.,*Proc. Natl. Acad. Sci.*

USA 89:205–6). It follows therefore that host cells containing an alternate means of processing sucrose will not be suitable in the present method.

It is contemplated that any host cell that lacks the genetic machinery to metabolize sucrose will be suitable in the present invention. Preferred host cells will belong to the genus Bacillus and lack either the sacB gene or the sacA gene, necessary for sucrose metabolism in wild-type Bacillus. Bacillus species suitable as host cells include but are not limited to *B. cereus, B. subtilis, B. pasteurii, B. circulans, B. amyloliqufaciens, B. oleronius, B. stearothermophilus, B. thuringiensis, B. licheniformis, B. natto, B. intermedius, B. megaterium, B. firmus, B. macerans, B. curdlanolyticus, B. infernus, B. anthracis, B. pumilus,* and *B. borstelensis*. Preferred in the present invention is *B. subtilis* (BE1510: trpC2, metB10, lys-3, $\Delta$aprE66, $\Delta$npr-82, sacB::ermC, sacA::phleo).

Vector Construction:

The present invention provides a positive selection vector containing; the sacB[BamP]W29 structural gene encoding a Bacillus levansucrase with a mutant signal peptide; a gene encoding antibiotic resistance; a Bacillus origin of replication for maintaining the vector in the host cell as multicopy; and suitable regulatory sequences necessary for the expression of the sacB[BamP]W29 gene.

Construction of the selection vector proceeded first by the isolation of the sacB[BamP]W29 gene. The sacB[BamP] W29 gene was extracted from the *E. coli* host, DH5α (pBE517) (Borchert et al., supra) where the W29 mutant gene was continined within the plasmid pBE517. Plasmid DNA was recovered and purified by standard methods (Sambrook supra). Plasmid pBE517 contains the sacB [BamP]W29 gene, origins of replication for Bacillus and *E. coli*, and a gene encoding chloramphenicol acetyltransferase (cat). pBE517 was digested with the restriction enzymes Kpn1 and Nde1 and the resulting fragment was ligated with a 1.2 kb fragment obtained from pUS19 containing a gene for specinomycin (spm) resistance to form pMGB161 (FIG. 2). pMGB161 is a shuttle vector useful for transferring between *E. coli* and Bacillus. pMGB161 was then digested with Sac1/Nco1 where subsequent ligation of the blunt ends produced pMGB161$\Delta$cat1 having only sacB[BamP]W29, the Bacillus origin of replication and the spm gene.

Although pMGB161$\Delta$cat1 is preferred over pMGB161 as a positive selection vector due to its smaller size, it is contemplated that both vectors will function equally well in the transformation of Bacillus hosts with heterologus DNA.

Regulatory sequences encoding a promoter and a ribosome binding site may be obtained from any single gene which is useful in driving the sacB[BamP]W29 gene. It is understood that the regulatory DNA sequences encoding the promoter and ribosome binding site may be obtained from cells other than the host cell. These regulatory DNA sequences can be isolated by means well known to those in the art and illustrative examples are documented in the literature. See Biotechnology Handbook 2 Bacillus, C. R. Harwood, Ed., Plenum Press, New York, N.Y. (1989). The promoters in the DNA sequences may be either constitutive or inducible allowing for facile regulation of the vector.

Cloning and Expression and Positive Selection of DNA Inserts:

pMGB161$\Delta$cat1 was used for insertion of heterologus DNA into suitable host cells. As has been mentioned, suitable host cells are unable to metabolize sucrose. In Bacillus this is generally due to a defective or absent sacB or sacA genes which regulate sucrose metabolism in the wild-type bacteria. Cells preferred in the present invention are the *Bacillus subtilis* (BE1510: trpC2, metB10, lys-3, $\Delta$aprE66, $\Delta$npr-82, sacB::ermC, sacA::phleo).

Within the sacB[BamP]W29 gene are numerous compatible cloning sites useful for the insertion of heterologus DNA. The engineering of DNA fragments with restriction sites convenient for insertion into vector DNA is common and well known in the art and examples may be found described by Sambrook et al., supra. Assistance for determining the compatibility of restriction sites may be obtained from the *Restriction Fragment Compatibility Table* of the New England Biolabs 1988–1989 Catalog, New England Biolabs Inc., Beverly, Mass. 01915 (1988).

Figure 4:
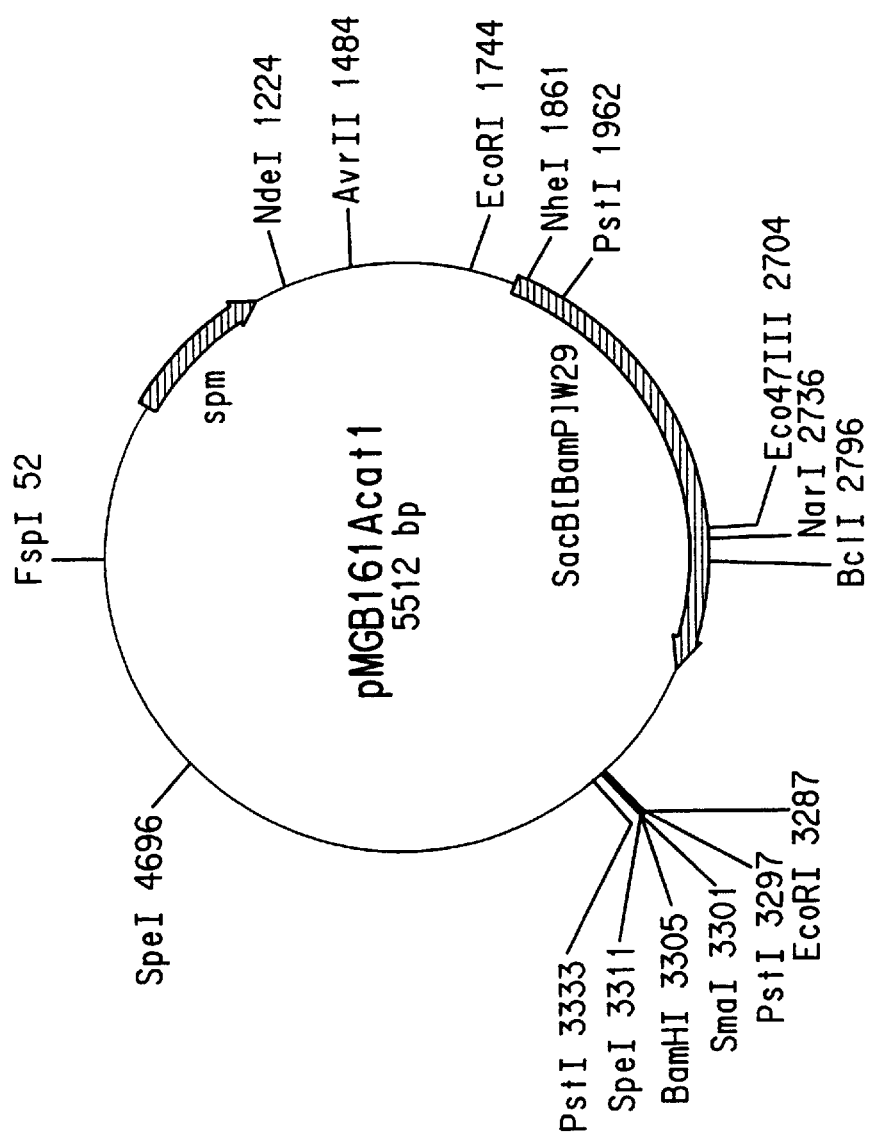
FIG. 4 is a restriction map of pMGB161Δcat1.

Insertion of foreign DNA into one of the cloning sites within sacB[BamB]W29 results in the inactivation of the W29 mutation and reverses lethality in the host cell. It is understood that any insertion at any point in the gene is expected to produce this result. For the purposes of the present invention insertion of DNA at the Bcl1 site is preferred (FIG. 4). Alternative insertions may also be made at the Nhe1 site (FIG. 4) and the Eco47III site (FIG. 4).

To examine the utility of the vector, DNA was isolated from two different sources and inserted into the appropriate sites in the vector. Genomic DNA was isolated from *B. stearothermophilus* and digested with Sau3A. The partial digest resulted in random 0.5 to 20 kb fragments that were then cloned into the Bcl1 site in the sacB[BamP]W29 gene contained within pMGB161$\Delta$cat. Alternatively, the *B. amyloliquifaciens* apr structural gene encoding the alkaline protease gene was obtained by PCR using the appropriate primers and also inserted into the Bcl1 site.

Vectors containing the foreign DNA were use to transform competent *B. subtilis*. Transformants grown both in the medium containing spectinomycin alone or sucrose with spectinomycin were compared for actively growing colonies and analyzed for the presence of inserts. Transformants screened for antibiotic resistance alone produced at least four times as many colonies as those screened for spectinomycin resistance and growth in the presence of sucrose. However, colonies that grew in the presence of sucrose had about a 95% to 100% incidence of transformation with inserts as compared with less than a 1% incidence of insert transformation for colonies screened only for antibiotic resistance.

The following examples are meant to exemplify the invention but should not be construed as limiting in any way.

EXAMPLES

Example 1

Demonstration that sacB[BamP]W29 Inhibits Growth of *B. subtilis* in the Presence of Sucrose Effect of sacB[BamP]W29 on Growth of *B. subtilis* in Liquid Medium with Sucrose BE1510(pBE504) containing the wild type sacB[BamP] and BE1510(pBE517) containing the W29 sacB mutation were inoculated into 20 ml of LB containing 5 µg/ml chloramphenicol or the same medium with 5% sucrose. The cultures were incubated in 300 ml sidearm flasks at 30° C. with shaking. Growth of the bacteria was monitored by measuring culture turbidity with a Klett-Summerson calorimeter fitted with a green filter.

Figure 1B:
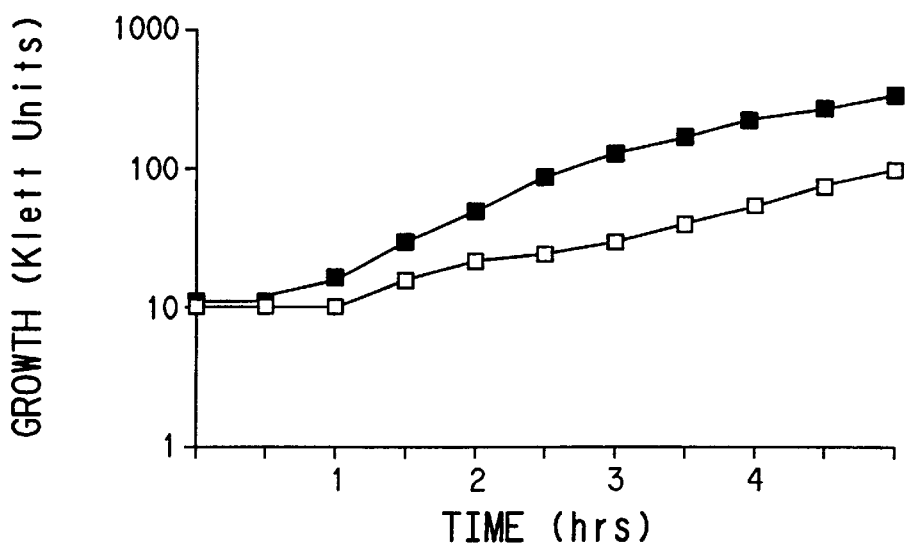

The data comparing the growth of BE1510(pBE504) and BE1510(pBE517) with and without sucrose is given in FIG. 1, where:

A)

BE1510(pBE504) with sucrose (□);
BE1510(pBE504) without sucrose (■).

B)

BE1510(pBE517) with sucrose (□);

BE1510(pBE517) without sucrose (■).

As can be seen in FIG. 1, pBE504 had no noticeable effect on growth of the bacteria in either medium (FIG. 1A). The growth of BE1510(pBE517) in medium without sucrose was indistinguishable from BE1510(pBE504). BE1510 (pBE517) had a doubling time of 40 minutes in medium without sucrose. However, BE1510(pBE517) required 75 minutes to double in medium with 5% sucrose. Thus, the growth rate of BE1510(pBE517) was significantly depressed in medium containing 5% sucrose. In addition, the final cell density of BE1510(pBE517) was 400 Klett units in LB whereas the final cell density in LB+5% sucrose was only 100 Klett units.

Effect of sacB[BamP]W29 on Growth of *B. subtilis* on Agar Medium with Sucrose

A single colony of BE1510(pBE504) or BE1510 (pBE517) was inoculated into 20 ml of LB containing 5 μg/ml chloramphenicol. The cultures were incubated in 300 ml sidearm flasks at 37° C. with shaking until the bacteria reached a density of 82 Klett units, as determined with a Klett-Summerson calorimeter fitted with a green filter. Using methods familiar to those skilled in the art, the viability of the bacteria on LB agar containing 5 μg/ml chloramphenicol or the same medium with 5% sucrose was evaluated by determining the number of colony-forming units (CFU) per ml of the liquid cultures for each agar medium.

As shown in Table 1, the viability of BE1510(pBE504) on agar medium was unaffected by sucrose. In contrast, the number of CFUs for BE1510(pBE517) was reduced 1000-fold by the presence of 5% sucrose in the agar medium. Thus, sucrose strongly inhibited growth on agar by bacteria containing sacB[BamP]W29.

TABLE 1

| Strain | LB agar supplement | CFU/ml |
| --- | --- | --- |
| BE1510(pBE504) | chloramphenicol | $5.1 \times 10^6$ |
| | chloramphenicol + sucrose | $5.7 \times 10^6$ |
| BE1510(pBE517) | chloramphenicol | $3.0 \times 10^6$ |
| | chloramphenicol + sucrose | $1.2 \times 10^3$ |

Example 2

Construction of Cloning Vectors with sacB[BamP] W29

Figure 2:
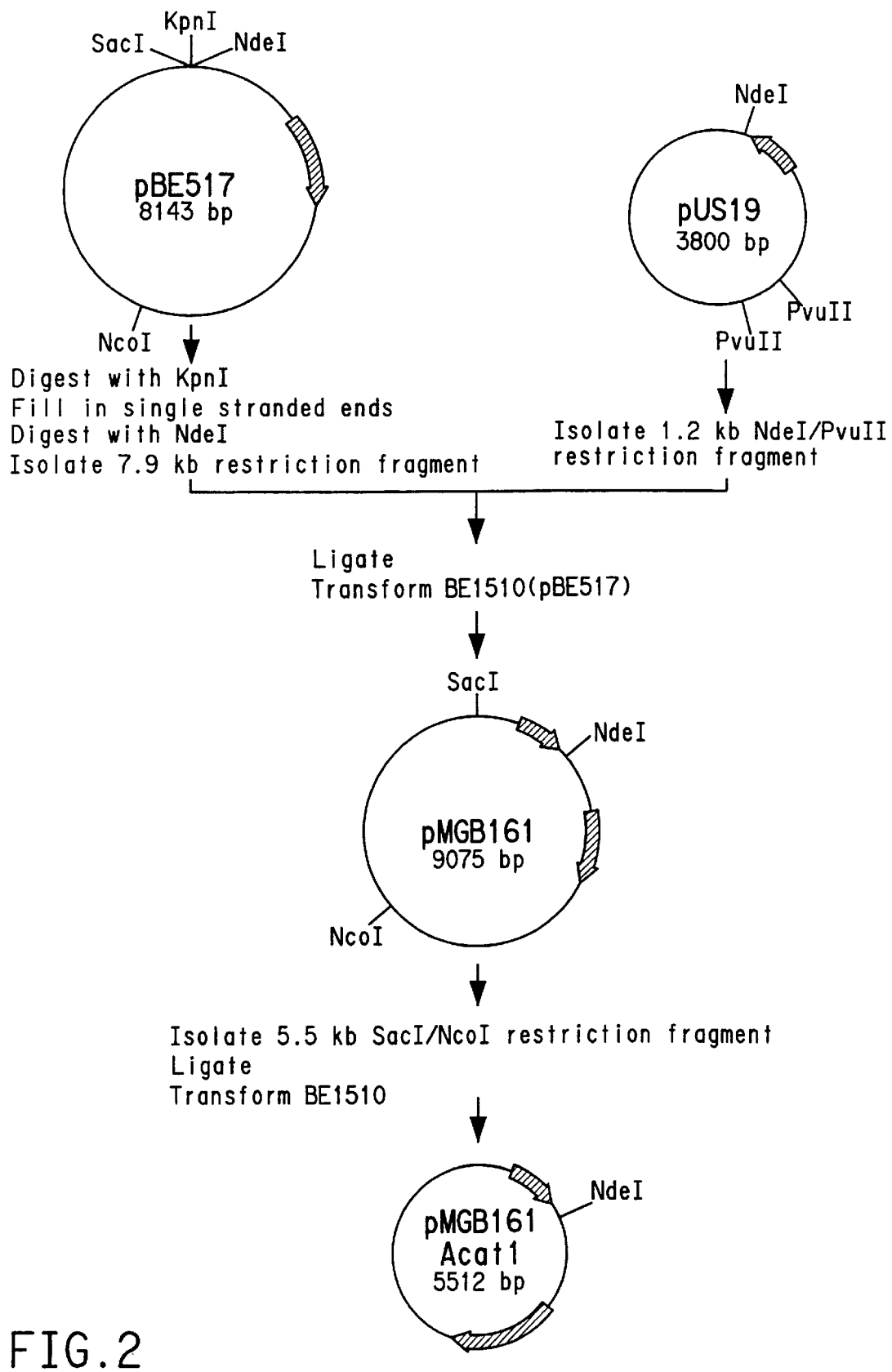
FIG. 2 illustrates the construction of pMGB161 and pMGB161Δcat1.

The plasmid vectors pMGB161 and pMGB161Δcat1 were constructed as outlined in FIG. 2. pMGB161 was constructed by cloning a PvuII/NdeI restriction fragment of pUS19 with a spectinomycin resistance gene into pBE517. Since pBE517 has origins for replication in *E. coli* and *B. subtilis*, pMGB161 is a shuttle vector for these bacteria. The *E. coli* origin of replication and a portion of a chloramphenicol acetyltransferase (cat) gene were deleted from pMGB161 to yield pMGB161Δcat1.

Construction of pMGB161

Preparation of DNA—Plasmid pBE517

*E. coli* strain DH5a(pBE517) was streaked for isolated colonies on LB agar (Sambrook et al., ibid., p. A.1 and p. A.4) containing 50 μg/ml of ampicillin and incubated at 37° C. for 18 hours. The bacteria from the region of heaviest growth were suspended in 1 ml of STE buffer (0.1 M NaCl, 10 mM Tris-HCl pH8.0, 1 mM EDTA) and collected by centrifugation in a 1.5 ml microfuge tube. Plasmid DNA was extracted from the cell pellet using the commercially available Wizard Minipreps DNA Purification System (Promega Corporation, 2800 Woods Hollow Road, Madison, Mich. 53711-5399) according to manufacturer's instructions. The Plasmid DNA was recovered in 50 μl of TE buffer (10 mM Tris-HCl pH 8.0, 1 mM EDTA) and its concentration determined using methods well known to those skilled in the art.

pBE517 (5 μg) was digested with 20 units of KpnI (Promega) at 37° C. for 1 hour in 50 μl of 1× reaction buffer supplied by the manufacturer. The reaction was stopped by adding 10 μl of 0.5 M EDTA. The unit length, linearized plasmid DNA was extracted from the KpnI reaction buffer by using the commercially available Geneclean Kit (Bio 101 Inc., P.O. Box 2284, La Jolla, Calif. 92038-2284) according to manufacturer's instructions. The DNA was resuspended in 10 μl of water. The protruding 3' termini produced by KpnI were removed by treating the KpnI digested pBE517 with 20 units of T4 DNA polymerase (Promega) in 100 μl of reaction buffer (33 mM Tris-acetate pH 7.9, 66 mM potassium acetate, 100 mM magnesium acetate, 5 mM dithiothretol, 0.1 mg/ml bovine serum albumin, 0.1 mM of each deoxynucleoside triphosphate) at 37° C. for 5 minutes. The reaction was stopped by adding 10 μl of 0.5 M EDTA and heating the reaction at 70° C. for 10 minutes. The DNA was extracted from the T4 DNA polymerase reaction buffer by using the Geneclean Kit (Bio 101 Inc.). The DNA was resuspended in 10 μl of water. The now blunt ended DNA was digested with 40 units of NdeI (Promega) at 37° C. for 1 hour in 50 μl of 1× reaction buffer supplied by the manufacturer. The DNA was extracted from the NdeI reaction buffer by using the Geneclean Kit (Bio 101 Inc.). The DNA was resuspended in 10 μl of TE buffer. The two restriction fragments that resulted from digestion with NdeI were separated by electrophoresis at 100 volts for 30 minutes in a 0.8% agarose gel (8.3 cm×6.0 cm×0.5 cm) as described by Sambrook et al., ibid., p. 6.3–6.19. The 7.9 kb restriction fragment was extracted from the agarose gel using the Geneclean Kit (Bio 101 Inc.). The DNA was resuspended in 10 μl of TE buffer.

Preparation of the DNA—PvuII/NdeI Restriction Fragment of pUS19

Plasmid pUS19 is a derivative of plasmid ColE1 that contains a spectinomycin resistance gene (spm) [Benson and Haldenwang, J. Bacteriol. 175:2347–2356 (1993)]. Alkaline lysis and polyethylene glycol precipitation were used to extract pUS19 from *E. coli* strain RR1(pUS19) that was grown in 500 ml of LB containing 50 μg/ml ampicillin and chloramphenicol-amplified according to methods described in Sambrook et al., ibid., p. 1.33 and pp. 1.38–1.41.

pUS19 (10 μg) was digested with 48 units of PvuII (Promega) at 37° C. for 1 hour in 100 μl of 1× reaction buffer supplied by the manufacturer. The unit length, linearized plasmid DNA was precipitated from the PvuII reaction buffer with 7.5 M ammonium acetate and absolute ethanol using methods well known to those skilled in the art. The DNA was dissolved in 100 μl of 1× NdeI reaction buffer supplied by the manufacturer and cut with 80 units of NdeI (Promega) at 37° C. for 1 hour. The DNA was precipitated from the NdeI reaction buffer with 7.5 M ammonium acetate and absolute ethanol and was dissolved in 10 μl of TE buffer. The two fragments that resulted from digestion with NdeI were separated by electrophoresis at 100 volts for 30 minutes in a 0.8% agarose gel. The 1.2 kb PvuII/NdeI restriction fragment that contained spm was extracted from the agarose gel using a Geneclean Kit (Bio 101 Inc.). The DNA was resuspended in 10 ml of TE buffer.

Ligation of Restriction Fragments and Transformation of *B. subtilis* BE1510(pBE517)

The spm gene was inserted into pBE517 by incubating a ligation reaction [5 µl blunt-ended 7.9 kb KpnI/NdeI restriction fragment from pBE517, 2 µl 1.2 kb PvuII/NdeI restriction fragment from pUS19, 4 µl water, 2 µl commercially prepared 10× ligation buffer (New England Biolabs, Inc., 32 Tozer Road, Beverly, Mass. 01915-5599), 6 µl 50% polyethylene glycol 8000, 400 units T4 DNA Ligase (New England Biolabs, Inc.)] at 23° C. for 18 hours.

*B. subtilis* strain BE1510(pBE517) was made competent for transformation and 0.5 ml of competent cells were transformed with 10 µl of the ligated DNA according to procedures described in Harwood and Cutting, p. 67. After incubation with the DNA, the transformation cultures were diluted with 1 ml of Brain Heart Infusion (BHI; Difco, Detriot, Mich.) and incubated on a roller drum at 37° C. for 1 hour. The contents of each culture tube were concentrated 10-fold by centrifugation and spread onto tryptose blood agar base (TBAB; Difco) containing 100 µg/ml spectinomycin. The petri plates were incubated at 37° C. for 18 hours.

Characterization of Spectinomycin Resistant Transformants

Figure 3:
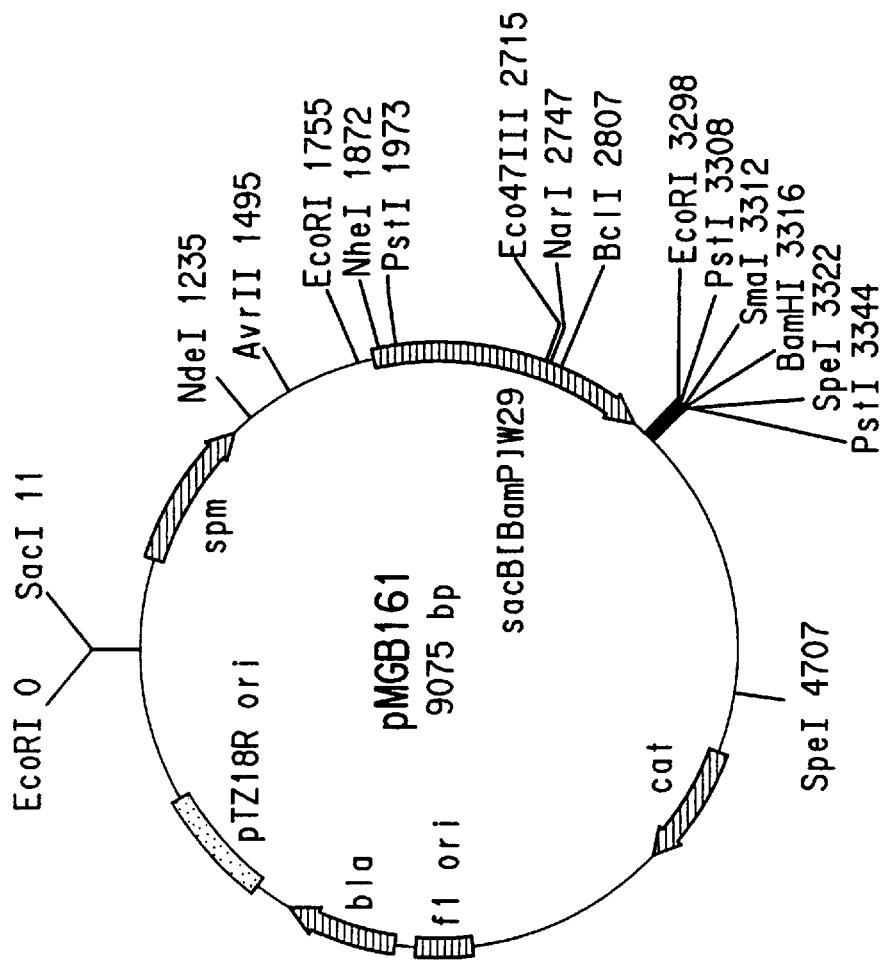
FIG. 3 is a restriction map of pMGB161.

Several spectinomycin resistant transformants were inoculated into 3 ml of BHI containing 100 µg/ml spectinomycin and incubated on a roller drum at 37° C. for 5 hours. Plasmid DNA was extracted from each culture using the Wizard Minipreps DNA Purification System. Samples of each plasmid preparation (10 µl) were digested with 12 units of EcoRI (Promega) in 50 µl total volume using reaction buffer supplied by the manufacturer. The resulting restriction fragments were analyzed by electrophoresis at 100 volts for 30 minutes in a 0.8% agarose gel. One plasmid that had restriction fragments of the expected sizes (5.7 kb, 1.7 kb, and 1.5 kb) was designated pMGB161. A detailed restriction map of pMGB161 is shown in FIG. 3.

Construction of pMGB161Δcat1

Alkaline lysis and polyethylene glycol precipitation were used to extract pMGB161 from BE1510(pMGB161) that was grown in 500 ml of LB containing 50 µg/ml ampicillin as described by Sambrook et al., ibid. pMGB161 (35 µg) was digested with 72 units of NcoI (Promega) at 37° C. for 1 hour in 100 µl of 1× reaction buffer supplied by the manufacturer. The unit length, linearized plasmid DNA was precipitated from the NcoI reaction buffer with 7.5 M ammonium acetate and absolute ethanol. The DNA was dissolved in 100 µl of 1× SacI reaction buffer supplied by the manufacturer and cut with 72 units of SacI (Promega) at 37° C. for 1 hour. The DNA was precipitated from the SacI reaction buffer with 7.5 M ammonium acetate and absolute ethanol and was dissolved in 35 µl of TE buffer. The two restriction fragments that resulted from digestion with NcoI and SacI were separated by electrophoresis at 100 volts for 45 minutes in a 0.8% agarose gel. The 5.7 kb NcoI/SacI restriction fragment that contained an origin for replication in *B. subtilis*, sacB[BamP]W29, and spm, was extracted from the agarose gel using a Geneclean Kit (Bio 101 Inc.). The DNA was resuspended in 60 µl of TE buffer.

The single stranded termini of the 5.7 kb restriction fragment were made blunt by treating the fragment with 100 units of T4 DNA polymerase (Promega) in 100 µl of reaction buffer (33 mM Tris-acetate pH 7.9, 66 mM potassium acetate, 100 mM magnesium acetate, 5 mM dithiothreotol, 0.1 mg/ml bovine serum albumin, 0.1 nM of each deoxynucleoside triphosphate) at 37° C. for 5 minutes. The reaction was stopped by adding 10 µl of 0.5 M EDTA and heating the reaction at 70° C. for 10 minutes. The reaction mixture was sequentially extracted one time with phenol/chloroform and chloroform using methods well known to those skilled in the art. The DNA was precipitated with 7.5 M ammonium acetate and absolute ethanol and was dissolved in 10 µl of water.

The 5.7 kb restriction fragment was circularized by incubating a ligation reaction (9 µl dissolved DNA, 1.5 µl commercially prepared 10× ligation buffer (New England Biolabs, Inc.), 4.5 µl 50% polyethylene glycol 8000, 400 units T4 DNA Ligase (New England Biolabs, Inc.)] at 23° C. for 20 hours. *B. subtilis* strain BE1510 was made competent for transformation and 0.5 ml of competent cells were transformed with 9 µl of ligated DNA according to procedures described in Harwood and Cutting, ibid. After incubation with the DNA, the transformation cultures were diluted with 1 ml of BHI and incubated on a roller drum at 37° C. for 1 hour. Samples of each culture (0.1 ml) were spread onto TBAB containing 100 µg/ml spectinomycin. The petri plates were incubated at 37° C. for 18 hours.

Several spectinomycin resistant, chloramphenicol sensitive transformants were inoculated into 3 ml of BHI containing 100 µg/ml spectinomycin and incubated on a roller drum at 37° C. for 5 hours. Plasmid DNA was extracted from each culture using the Wizard Minipreps DNA Purification System (Promega). Samples of each plasmid preparation (20 µl) were digested with 12 units of EcoRI (Promega) in 50 µl total volume using reaction buffer supplied by the manufacturer. The resulting restriction fragments were analyzed by electrophoresis at 100 volts for 45 minutes in a 0.8% agarose gel. One plasmid that had restriction fragments of the expected sizes (4.0 kb and 1.5 kb) was designated pMGB161Δcat1. A detailed restriction map of pMGB161Δcat1 is shown in FIG. 4.

Example 3

Use of pMGB161Δcat1 to Clone Random Restriction Fragments Derived From *B. stearothermophilus* Chromosome DNA Preparation of *B. stearothermophilus* DNA Bacillus Genetic Stock Center *B. stearothermophilus* strain 9A2 was grown in 25 ml of BHI for 6.5 hours at 60° C. with shaking. The bacteria were collected by centrifugation and resuspended in 2.5 ml of buffer (50 mM Tris, 10 mM EDTA, pH 8.0). Lysozyme was added to a final concentration of 200 µg/ml, and the resulting mixture was incubated at 37° C. for 15 minutes. Proteinase K and sodium dodecyl sulfate were added (final concentrations of 50 µg/ml and 0.5%, respectively), and the resulting mixture was incubated at 55° C. for 2 hours. The DNA was precipitated with 7.5 M ammonium acetate and absolute ethanol, and then dissolved in 1 ml TE buffer. The DNA was incubated with DNase free RNase (150 µg/ml final concentration) for 30 minutes at 23° C. Using methods well known to those skilled in the art, the DNA was extracted one time with an equal volume of phenol/chloroform, extracted one time with an equal volume of chloroform, and precipitated again with 7.5 M ammonium acetate and absolute ethanol. The isolated DNA was rinsed with 70% ethanol, air dried, and dissolved in 500 µl TE buffer.

*B. stearothermophilus* DNA (60 µg) was digested with 0.1 units of Sau3A (Promega) at 23° C. for 20 minutes in 50 µl of 1× reaction buffer supplied by the manufacturer. The resulting partial digest contained a semi-random collection of restriction fragments that were predominately 0.5 kb to 20 kb in size. The reaction mixture was sequentially extracted one time with phenol/chloroform, and chloroform using methods well known to those skilled in the art. The DNA was precipitated with 7.5 M ammonium acetate and absolute ethanol and was dissolved in 10 μl of TE buffer.

Cloning of *B. stearothermophilus* DNA into pMGB161Δcat1 pMGB161Δcat1 (8 μg) was digested with 20 units of BclI (Promega) at 50° C. for 1 hour in 200 μl of 1× reaction buffer supplied by the manufacturer. The reaction mixture was sequentially extracted one time with phenol/chloroform, and chloroform using methods well known to those skilled in the art. The DNA was precipitated with 7.5 M ammonium acetate and absolute ethanol and was dissolved in 10 μl of TE buffer.

The *B. stearothermophilus* DNA was inserted into pMGB161Δcat1 by incubating a ligation reaction [4.5 μl Sau3A partial digest of *B. stearothermophilus* DNA, 4.5 μl of BclI digested pMGB161Δcat1, 1 μl commercially prepared 10× ligation buffer (New England Biolabs, Inc.), 200 units T4 DNA Ligase (New England Biolabs, Inc.)] at 23° C. for 2.5 hours.

Competent cells of *B. subtilis* strain BE1510 (0.5 ml) were transformed with 10 μl the ligated DNA as described in Harwood and Cutting, p. 67. After incubation with the DNA, samples of the transformation culture and a similar control culture of cells that were not exposed to DNA were diluted with 1 μl of BHI and incubated on a roller drum at 37° C. for 1 hour. The cells were spread onto LB agar containing 100 μg/ml spectinomycin (LBAS) or LB agar containing 100 μg/ml spectinomycin and 5% sucrose (LBASS) to determine the number of transformants that were resistant to only spectinomycin or that were resistant to spectinomycin and sucrose. The petri plates were incubated at 30° C. for 20 hours.

As shown in Table 2, significantly fewer transformants were resistant to spectinomycin and sucrose than to spectinomycin alone. Ten transformants were picked from LBAS and ten transformants were picked from LBASS. The transformants from LBASS were grown in 3 ml of BHI containing 100 μg/ml spectinomycin and 5% sucrose with incubation on a roller drum at 37° C. for 5 hours. The transformants from LBAS were cultured in a similar manner except that the medium lacked sucrose. Plasmid DNA was extracted from each culture using the Wizard Minipreps DNA Purification System (Promega). Samples of each plasmid preparation (25 μl) were digested with 12 units of EcoRI (Promega) in a total volume of 50 μl using reaction buffer supplied by the manufacturer. The resulting restriction fragments were analyzed by electrophoresis at 100 volts for 30 minutes in a 0.8% agarose gel. An EcoRI digest of pMGB161Δcat1 yielded two bands corresponding to restriction fragments 3.7 and 1.4 kb in size. The 1.4 kb fragment contains the sacB[BamP]W29 sequence and will be altered in size if DNA has been cloned into the BclI restriction site of pMGB161Δcat1. EcoRI digests of the plasmids from all ten transformants that were picked from LBAS yielded two bands that were indistinguishable from the pMGB161Δcat1 EcoRI restriction fragments in size. Thus, none of the transformants derived from LBAS contained cloned *B. stearothermophilus* DNA. The EcoRI digests of the plasmids from the ten transformants that were picked from LBASS were similar to each other in that the 3.7 kb fragment was present in each digest but the 1.4 kb fragment was missing. In each case, the 1.4 kb fragment was replaced by one fragment larger than 1.4 kb or two fragments with a combined size larger than 1.4 kb. Thus, each of the ten transformants that were picked from LBASS contained plasmids with cloned inserts. As shown in Table 3, small inserts predominated among the examined transformants. However, it was evident that pMGB161Δcat1 can accommodate inserts as large as 6.3 kb.

TABLE 2

| Culture | LB agar supplement | Transformants/ml |
| --- | --- | --- |
| BE1510 only | spectinomycin | <10 |
|  | spectinomycin + sucrose | <10 |
| BE1510 + ligated DNA | spectinomycin | $2.6 \times 10^4$ |
|  | spectinomycin + sucrose | $6.9 \times 10^3$ |

TABLE 3

| Fragment Size | No. of transformants with fragment |
| --- | --- |
| 0.3 kb | 4 |
| 0.4 kb | 1 |
| 0.6 kb | 3 |
| 1.1 kb | 1 |
| 6.3 kb | 1 |

Example 4

Use of pMGB161Δcat1 to Clone Polymerase Chain Reaction (PCR) Amplified DNA Containing the *B. amyloliquifaciens* apr Gene Preparation of *B. amyloliquifaciens* DNA

*B. amyloliquifaciens* was grown in 25 ml of BHI for 5 hours at 37° C. with shaking. The bacteria were collected by centrifugation and resuspended in 3 ml of TE buffer. Lysozyme was added to a final concentration of 333 μg/ml, and the resulting mixture was incubated at 37° C. for 15 minutes. Proteinase K and sodium dodecyl sulfate were added (final concentrations of 50 μg/ml and 0.5%, respectively), and the resulting mixture was incubated at 55° C. for 2 hours. Using methods well known to those skilled in the art, the DNA was precipitated with 7.5 M ammonium acetate and absolute ethanol, dissolved in 2 ml TE buffer, extracted one time with an equal volume of phenol/chloroform, extracted one time with an equal volume of chloroform, precipitated again with 7.5 M ammonium acetate and absolute ethanol. The isolated DNA was rinsed with 70% ethanol, air dried, and dissolved in 1 ml TE buffer.

Amplification of the *B. amyloliquifaciens* apr Gene by the Polymerase Chain Reaction (PCR)

The promoter and coding sequence of the *B. amyloliquifaciens* apr gene were amplified by PCR using AmpliTaq DNA polymerase (Perkin Elmer) and a GeneAmp PCR Reagent Kit (Perkin Elmer) according to the manufacturer's directions. Two oligonucleotide primers of 30 bases each were synthesized for use in the PCR reactions. The sequences of the two 30mer oligonucleotide primers that were used in the reactions were based on the reported nucleotide sequence for the *B. amyloliquifaciens* apr gene [Vasantha et al., J. Bacteriol. 159:811–819 (1984)]. The primers were designed to flank the target sequence with BamHI restriction sites. The sequence of each primer is set forth below:

| Primer No. | Nucleotide Sequence |
|---|---|
| APR3 | CCC CCA AAA ATG GAT CCA AAC CGT TCG ACC SEQ ID NO 2 |
| APR4 | CGA TTA TGG AGC GGA TTG AGG ATC CGG AGG SEQ ID NO 3 |

The 100 μl PCR mixes contained 0.8 μg of *B. amyloliquefaciens* DNA. The final concentration of each primer in the PCR mixes was 1.0 mM. The reactions were performed in a GeneAmp PCR System 9600 thermocycler (Perkin Elmer) with 40 cycles consisting of a melting step (94° C. for 1 minute), a primer annealing step (45° C. for 1 minute), and a primer extension step (72° C. for 2 minutes). After completion of the last cycle, the amplified DNA was separated from unincorporated primers by using a commercially available Wizard PCR Preps DNA Purification System kit (Promega).

The DNA from two separate amplification reactions was combined (8 μg total) and digested with 20 units of BamHI (Promega) at 37° C. for 1 hour in 100 μl of 1× reaction buffer supplied by the manufacturer. The DNA was precipitated from the BamHI reaction buffer with 7.5 M ammonium acetate and absolute ethanol and was dissolved in 5 μl of TE buffer. The BamHI digested DNA was analyzed by electrophoresis at 100 volts for 30 minutes in a 0.8% agarose gel. A 1.5 kb fragment was extracted from the agarose gel using a Geneclean Kit (Bio 101 Inc.). The DNA was resuspended in 10 μl of TE buffer.

Cloning of Amplified DNA into pMGB161Δcat1 pMGB161Δcat1 (10 μg) was digested with 40 units of BclI (Promega) at 50° C. for 1 hour in 50 μl of 1× reaction buffer supplied by the manufacturer. The DNA was extracted from the BclI reaction buffer by using a Geneclean Kit (Bio 101 Inc.). The DNA was resuspended in 10 μl of TE buffer. The BclI digested pMGB161Δcat1 (10 ml) and BamHI digested 1.5 kb fragment (10 μl) were combined, precipitated with 7.5 M ammonium acetate and ethanol, and resuspended in 10 μl of 1× ligation buffer containing 200 units of T4 DNA ligase (New England Biolabs, Inc.). The ligation reaction was incubated at 23° C. for 20 hours.

Competent cells of *B. subtilis* strain BE1510 (0.5 ml) were transformed with 10 μl of the ligated DNA as described in Harwood and Cutting, p. 67. After incubation with the DNA, samples of the transformation culture and a similar control culture of cells that were not exposed to DNA were diluted with 1 ml of BHI and incubated on a roller drum at 37° C. for 1 hour. The cells were spread onto LBAS or LBASS to determine the number of transformants that were resistant to only spectinomycin or that were resistant to spectinomycin and sucrose. The petri plates were incubated at 30° C. for 20 hours.

TABLE 4

| Culture | Plating Medium | Transformants/ml |
|---|---|---|
| BE1510 only | spectinomycin | <10 |
|  | spectinomycin + sucrose | <10 |
| BE1510 + ligated DNA | spectinomycin | $3.4 \times 10^4$ |
|  | spectinomycin + sucrose | $6.0 \times 10^2$ |

As shown in Table 4, significantly fewer transformants were resistant to spectinomycin and sucrose than to spectinomycin alone. Several transformants were picked from the LBAS or the LBASS and patched to TBAB containing spectinomycin and 1% skim milk. Patches that are surrounded by a clear halo on medium containing skim milk are positive for production of extracellular protease (Vasantha, N., et al., *J. Bacterial.* 159, 811, (1984)). The petri plates were incubated at 37° C. for 18 hours.

TABLE 5

| LB agar supplement | No. Patched | No. Protease Positive |
|---|---|---|
| spectinomycin | 50 | 0 |
| spectinomycin + sucrose | 50 | 23 |

As shown in Table 5, none of the transformants that were resistant to only spectinomycin were protease positive whereas almost half of the spectinomycin/sucrose resistant transformants were also protease positive. Four protease positive transformants were inoculated into 3 ml of BHI containing 100 μg/ml spectinomycin and 5% sucrose and incubated on a roller drum at 37° C. for 5 hours. Plasmid DNA was extracted from each culture using the Wizard Minipreps DNA Purification System. Samples of each plasmid preparation (20 μl) were digested with 12 units of EcoRI (Promega) in 50 μl total volume using reaction buffer supplied by the manufacturer. The resulting restriction fragments were analyzed by electrophoresis at 100 volts for 45 minutes in a 0.8% agarose gel. The plasmid from each of the four protease positive transformants contained a cloned insert of the expected size (1.5 kb).

Example 5

Inactivation of the Polymerase Activity of the sacB [BamP]W29 Gene Product

Chambert and Petit-Glatron [*Biochem. J.* 279:35–41 (1991)] demonstrated that converting the arginine in position 331 of levansucrase ($Arg^{331}$) to leucine (Leu) inactivates the polymerase activity of the enzyme. Therefore, the polymerase activity of the sacB[BamP]W29 gene product was inactivated in a similar manner to demonstrate that the sacB[BamP]W29 was responsible for inhibiting *B. subtilis* growth in the presence of sucrose.

Modification of sacB[BamP]W29 by Site Directed Mutagenesis

A portion of the sacB[BamP]W29 was amplified by polymerase chain reaction (PCR) using AmpliTaq DNA polymerase (Perkin Elmer) and a GeneAmp PCR Reagent Kit (Perkin Elmer) according to the manufacturer's directions. Plasmid pMGB161Δcat1 was used as template DNA. (pMGB161Δcat1 is a derivative of pBE517. Construction of pMGB161Δcat1 is described under Example 2 and is illustrated in FIG. 2. A pMGB161Δcat1 restriction map is illustrated in FIG. 4). Two oligonucleotide primers were synthesized for use in the PCR reactions. The sequences of the two oligonucleotide primers that were used in the reactions were based on the reported nucleotide sequences for the *B. amyloliquifaciens* sacB gene [Tang et al., Gene 96:89–93 (1990)] and the polylinker region of pBE504 (Borchert and Nagarajan, ibid.). The primers were designed to allow amplification of a region of pMGB161Δcat1 that included the 473 base pairs between the BssHII restriction site and BamHI restriction site. Primer MB3 overlapped Arg codon 331 of sacB[BamP]W29 and was designed to convert codon 331 into a Leu codon in the amplified DNA. The sequence of each primer is set forth below:

| Primer No. | Nucleotide Sequence |
|---|---|
| MB2 | AGT GGA TCC CCC GGG CTG CAG GAA TTC ACC SEQ ID NO 4 |
| MB3 | GAG CGC GCG AAT GTT TTC AAA ATG AAC GGC AAA TGG TAC TTG TTC ACT GAT TCA CTC GGT TC SEQ ID NO 5 |

The 100 μl PCR mixes contained 1 ng of pMGB161Δcat1 DNA that had been digested with NheI. The final concentration of each primer in the PCR mixes was 1.5 mM. The reactions were performed in a GeneAmp PCR System 9600 thermocycler (Perkin Elmer) with 40 cycles consisting of a melting step (94° C. for 1 minute), a primer annealing step (45° C. for 1 minute), and a primer extension step (72° C. for 2 minutes). After completion of the last cycle, the amplified DNA was separated from unincorporated primers by using a commercially available Wizard PCR Preps DNA Purification System kit (Promega).

All of the amplified DNA from one reaction was digested with 10 units of BssHII (Promega) at 50° C. for 1 hour in 100 μl of 1× reaction buffer supplied by the manufacturer. The digestion at was continued at 37° C. for 1 hour after adding 10 units of BamHI (Promega). Using methods well known to those skilled in the art, the reaction mix was extracted one time with an equal volume of phenol/chloroform and extracted one time with an equal volume of chloroform. The DNA was precipitated with 7.5 M ammonium acetate and absolute ethanol. The isolated DNA was dissolved in 10 μl TE buffer.

Plasmid pMGB161 (10 μg) was digested with BssHI and BamHI as described in the previous paragraph. (pMGB161 is a derivative of pBE517. Construction of pMGB161 is described under Example 2 and is illustrated in FIG. 2. A pMGB161 restriction map is illustrated in FIG. 3.) The BssHII/BamHI DNA was precipitated with 7.5 M ammonium acetate and absolute ethanol. The two fragments that resulted from digestion with BssHII and BamHI were separated by electrophoresis at 100 volts for 30 minutes in a 0.8% agarose gel. A 8.6 kb BssHII/BamHI restriction fragment was extracted from the agarose gel using a Geneclean Kit (Bio 101 Inc.). The DNA was resuspended in 20 μl of TE buffer.

The BssHII/BamHI digested PCR amplified DNA was joined to the 8.6 kb BssHII/BamHI pMGB161 restriction fragment in a ligation reaction [2 μl 8.6 kb BssHII/BamHI pMGB161 restriction fragment, 5 μl BssHII/BamHI digested PCR amplified DNA, 2 μl water, 1 μl commercially prepared 10× ligation buffer (New England Biolabs, Inc., 32 Tozer Road, Beverly, Mass. 01915-5599), and 200 units T4 DNA Ligase (New England Biolabs, Inc.)]. The reaction was incubated at 23° C. for 18 hours. The entire ligation mix was used to transform commercially prepared E. coli strain RR1 (BRL/Life Technologies, Inc., Gaithersburg, Md. 20877) according to a standard procedure [Ausubel et al. (eds.), Current Protocols in Molecular Biology, p. 1.8.1–p. 1.8.3 John Wiley and Sons, New York] with selection for ampicillin resistance. One typical transformant was designated RR1(pMGB165).

RR1(pMGB165) was inoculated into 3 ml of LB containing 50 μg/ml ampicillin and incubated on a roller drum at 37° C. for 6 hours. Plasmid DNA was extracted from the culture using the Wizard Minipreps DNA Purification System. B. subtilis strain BE1510 was made competent for transformation and 0.5 ml of competent cells were transformed with 10 μl of the plasmid preparation according to procedures described in Harwood and Cutting, p. 67. After incubation with the DNA, the transformation cultures were diluted with 1 ml of Brain Heart Infusion (BHI; Difco, Detriot, Mich.) and incubated on a roller drum at 37° C. for 1 hour. The contents of each culture tube were concentrated 10-fold by centrifugation and spread onto tryptose blood agar base (TBAB; Difco) containing 100 μg/ml spectinomycin. The petri plates were incubated at 37° C. for 18 hours.

One transformant, BE1510(pMGB165), was inoculated into 3 ml of BHI containing 100 μg/ml spectinomycin and incubated on a roller drum at 37° C. for 6 hours. Plasmid DNA was extracted from the culture using the Wizard Minipreps DNA Purification System. A sample of the plasmid preparation (25 μl) was digested with 12 units of EcoRI (Promega) in 50 μl total volume using reaction buffer supplied by the manufacturer. The resulting restriction fragments were analyzed by electrophoresis at 100 volts for 30 minutes in a 0.8% agarose gel. pMGB165 had restriction fragments of the expected sizes (5.7 kb, 1.7 kb, and 1.5 kb).

Effect of Changing $Arg^{331}$ to Leu in sacB[BamP]W29

A single colony of BE1510(pMGB161) or BE1510 (pMGB165) was inoculated into 20 ml of LB containing 5 μg/ml chloramphenicol. The cultures were incubated in a 300 ml sidearm flask at 37° C. with shaking until the bacteria reached a density of approximately 85 Klett units, as determined with a Klett-Summerson calorimeter fitted with a green filter. The viability of the bacteria on LB agar containing 5 μg/ml chloramphenicol or the same medium with 5% sucrose was evaluated by determining the number CFUs per ml of the liquid cultures for each agar medium.

As shown in Table 6, the number of CFUs for BE1510 (pMGB161) was reduced 1000-fold by the presence of 5% sucrose in the agar medium. In contrast, the viability of BE1510(pMGB165) on agar medium was unaffected by sucrose. Thus, the polymerase activity of the sacB[BamP] W29 gene product was necessary for inhibition of growth on medium with sucrose by sacB[BamP]W29. Furthermore, this experiment suggested that inactivation of sacB[BamP] W29 could be used to select for growth of colonies of B. subtilis with cloned inserts in sacB[BamP]W29.

TABLE 6

| Strain | LB agar supplement | CFU/ml |
|---|---|---|
| BE1510(pMGB161) | chloramphenicol | $3.0 \times 10^6$ |
|  | chloramphenicol + sucrose | $3.1 \times 10^3$ |
| BE1510(pMGB165) | chloramphenicol | $5.1 \times 10^6$ |
|  | chloramphenicol + sucrose | $2.7 \times 10^6$ |

What is claimed is:

1. A method for the positive selection of Gram positive bacterial host cells transformed with heterologus DNA comprising:
   (i) constructing a positive selection vector comprising:
      (a) a levansucrase gene encoding an active levansucrase polymerase said gene having a signal peptide processing mutation causing a reduction in signal peptide processing, the gene further comprising compatible restriction sites useful for the insertion of heterologous DNA;
      (b) a gene encoding antibiotic resistance;
      (c) a host specific origin of replication for maintaining the vector as multicopy; and
      (d) suitable regulatory sequences for the regulation and expression of the levansucrase gene;
   (ii) cloning heterologous DNA into said compatible restriction sites of said levansucrase gene wherein the levansucrase polymerase activity is destroyed;
   (iii) transforming a competent Gram positive host cell with the vector of step (ii) wherein said host cell does not possess the ability to metabolize sucrose;
   (iv) incubating said transformed host cells in the presence of a suitable growth medium containing sucrose; and
   (v) isolating transformants which grow in the presence of sucrose.

2. The method of claim 1 wherein said Gram positive host cell is selected from the group consisting of Bacillus sp., Rhodococcus sp., Nocardia sp., Streptomyces sp., Streptococcus sp., Staphylococcus sp., Corynebacterium sp., and Clostridium sp.

3. The method of claim 2 wherein the Gram positive host cell is selected from the group consisting of *Bacillus subtilis, Bacillus pumilus, Bacillus loceniformis, Bacillus amyloliquifaciens, Bacillus thurgiensis, Bacillus stearothermophilus* and *Bacillus sphearicus*.

4. The method of claim 3 wherein said Gram positive host cell lacks either the sacB gene or sacA gene, or both the sacA gene and the sacB gene.

5. The method of claim 3 wherein the Gram positive host cell is *Bacillus subtilis*.

6. The method of claim 1 wherein the gene having a signal peptide processing mutation contains an amino acid at the (−1) position selected from the group consisting of tryptophan, arginine and proline.

7. The method of claim 1 wherein the gene having a signal peptide processing mutation contains an amino acid at the (−3) position selected from the group consisting of tryptophan, arginine and proline.

8. A method for the positive selection of Bacillus sp. hosts transformed with heterologous DNA comprising:

(i) constructing a positive selection vector comprising;
   (a) a sacB[BamP]W29 gene encoding an active levansucrase polymerase said gene having a signal peptide processing mutation causing a reduction in signal peptide processing, the gene further comprising compatible restriction sites useful for the insertion of heterologous DNA;
   (b) a gene encoding antibiotic resistance;
   (c) a Bacillus origin of replication for maintaining the vector as multicopy;
   (d) suitable regulatory sequences for the regulation of expression of the sacB[BamP]W29 gene;
(ii) cloning heterologous DNA into said compatible restriction sites of said sacB[BamP]W29 gene;
(iii) transforming a competent Bacillus host cell with the vector of step (ii) wherein said host cell does not possess the ability to metabolize sucrose;
(iv) incubating said transformed host cells in the presence of a suitable growth medium containing sucrose; and
(v) isolating transformants which grow in the presence of sucrose.

9. The method of claim 8 wherein said host cell lacks either the sacB gene or sacA gene or both the sacB gene and the sacA gene.

10. A positive selection vector for the positive selection of Gram positive bacterial host cells transformed with heterologus DNA comprising:
   (i) a levansucrase gene encoding an active levansucrase polymerase said gene having a signal peptide processing mutation causing a reduction in signal peptide processing, the gene further comprising compatible restriction sites useful for the insertion of heterologous DNA;
   (ii) a gene encoding antibiotic resistance;
   (iii) a host specific origin of replication for maintaining the vector as multicopy; and
   (iv) suitable regulatory sequences for the regulation of expression of the levansucrase gene.

11. The vector of claim 10 wherein said levansucrase gene is isolated from Bacillus sp.

12. The vector of claim 10 wherein the origin of replication for maintaining the vector as multicopy is specific to Bacillus sp.

13. The vector of claim 10 wherein the gene having the signal peptide processing mutation contains an amino acid at the (−1) position selected from the group consisting of tryptophan, arginine and proline.

14. The vector of claim 10 wherein the gene having the signal peptide processing mutation has the nucleic acid sequence corresponding to SEQ ID NO.:1.

15. The vector of claim 10 wherein the gene having a signal peptide processing mutation contains an amino acid at the (−3) position selected from the group consisting of tryptophan, arginine and proline.

16. A transformed *Bacillus subtilis* host cell containing the positive selection vector of claim 10 having the ATCC number ATCC 69945.

17. A transformed *Bacillus subtilis* host cell containing the positive selection vector of claim 10 having the ATCC number ATCC 69946.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 3305 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO:1:

```
CGCTGGCGTA ATAGCGAAGA GGCCCGCACC GATCGCCCTT CCCAACAGTT GCGCAGCCTG      60

AATGGCGAAT GGCGATTTTC GTTCGTGAAT ACATGTTATA ATAACTATAA CTAATAACGT     120

AACGTGACTG GCAAGAGATA TTTTTAAAAC AATGAATAGG TTTACACTTA CTTTAGTTTT     180

ATGGAAATGA AAGATCATAT CATATATAAT CTAGAATAAA ATTAACTAAA ATAATTATTA     240

TCTAGATAAA AAATTTAGAA GCCAATGAAA TCTATAAATA AACTAAATTA AGTTTATTTA     300

ATTAACAACT ATGGATATAA AATAGGTACT AATCAAAATA GTGAGGAGGA TATATTTGAA     360

TACATACGAA CAAATTAATA AAGTGAAAAA AATACTTCGG AAACATTTAA AAAATAACCT     420

TATTGGTACT TACATGTTTG GATCAGGAGT TGAGAGTGGA CTAAAACCAA ATAGTGATCT     480

TGACTTTTTA GTCGTCGTAT CTGAACCATT GACAGATCAA AGTAAAGAAA TACTTATACA     540

AAAAATTAGA CCTATTTCAA AAAAAATAGG AGATAAAAGC AACTTACGAT ATATTGAATT     600

AACAATTATT ATTCAGCAAG AAATGGTACC GTGGAATCAT CCTCCCAAAC AAGAATTTAT     660

TTATGGAGAA TGGTTACAAG AGCTTTATGA ACAAGGATAC ATTCCTCAGA AGGAATTAAA     720

TTCAGATTTA ACCATAATGC TTTACCAAGC AAAACGAAAA AATAAAAGAA TATACGGAAA     780

TTATGACTTA GAGGAATTAC TACCTGATAT TCCATTTTCT GATGTGAGAA GAGCCATTAT     840

GGATTCGTCA GAGGAATTAA TAGATAATTA TCAGGATGAT GAAACCAACT CTATATTAAC     900

TTTATGCCGT ATGATTTTAA CTATGGACAC GGGTAAAATC ATACCAAAAG ATATTGCGGG     960

AAATGCAGTG GCTGAATCTT CTCCATTAGA ACATAGGGAG AGAATTTTGT TAGCAGTTCG    1020

TAGTTATCTT GGAGAGAATA TTGAATGGAC TAATGAAAAT GTAAATTTAA CTATAAACTA    1080

TTTAAATAAC AGATTAAAAA AATTATAAAA AAATTGAAAA AATGGTGGAA ACACTTTTTT    1140

CAATTTTTTT GTTTTATTAT TTAATATTTG GGAAATATTC ATTCTAATTG GTAATCAGAT    1200

TTTAGAAAAC AATAAACCCT TGCATATGCC GCGATCGTGT TTATCATCAT TTCGGAACG    1260

CTCATCGCTT TTTATTGCTA TTTGGAAAGC CTGAAATATC TGAGTGCCTC TGAAACCAGC    1320

CTCCTCGCCT GTGCAGAGCC GCTGTCAGCA GCTTTTTTAG CGGTGATCTG GCTGCATGTT    1380

CCCTTCGGAA TATCAGAATG GCTGGGTACT TTACTGATTT TAGCCACCAT CGCTTATTAT    1440

CTATCAAGAA AAAATAACCT CTCTTTTTTT AGAGAGGTTT TTCCCTAGGC CTGAAGCACC    1500

CTTTAGTCTC AATTACCCAT AAATTAAAAG GCCTTTTTTC GTTTTACTAT CATTCAAAAG    1560

AGGAAAATAG ACCAGTTGTC AATAGAATCA GAGTCTAATA GAATGAGGTC GAAAAGTAAA    1620

TCACGCAGGA TTGTTACTGA TAAAGCAGGC AAGACCTAAA ATGTGTTAAG GGCAAAGTGT    1680

ATTCTTTGGC GTCATCCCTT ACATATTTTG GGTCTTTTTT TCTGTAACAA ACCTGCCATC    1740
```

```
CATGAATTCG GGAGGATCGA AACGGCAGAT CGCAAAAACA GTACATACAG AAGGAGACAT    1800

GAACATGAAC ATCAAAAAAA TTGTAAAACA AGCCACAGTA CTGACTACGT TTACTGCACT    1860

GCTAGCAGGA GGAGCAACTC AAGCCTTCTG GAAAGAAAAT AACCAAAAAG CATACAAAGA    1920

AACGTACGGC GTCTCTCATA TTACACGCCA TGATATGCTG CAGATCCCTA ACAGCAGCA     1980

AAACGAAAAA TACCAAGTGC CTCAATTCGA TCAATCAACG ATTAAAAATA TTGAGTCTGC    2040

AAAAGGACTT GATGTGTCCG ACAGCTGGCC GCTGCAAAAC GCTGACGGAA CAGTAGCAGA    2100

ATACAACGGC TATCACGTTG TGTTTGCTCT TGCGGGAAGC CCGAAAGACG CTGATGACAC    2160

ATCAATCTAC ATGTTTTATC AAAAGGTCGG CGACAACTCA ATCGACAGCT GGAAAAACGC    2220

GGGCCGTGTC TTTAAAGACA GCGATAAGTT CGACGCCAAC GATCCGATCC TGAAAGATCA    2280

GACGCAAGAA TGGTCCGGTT CTGCAACCTT TACATCTGAC GGAAAAATCC GTTTATTCTA    2340

CACTGACTAT TCCGGTAAAC ATTACGGCAA ACAAAGCCTG ACAACAGCGC AGGTAAATGT    2400

GTCAAAATCT GATGACACAC TCAAAATCAA CGGAGTGGAA GATCACAAAA CGATTTTTGA    2460

CGGAGACGGA AAAACATATC AGAACGTTCA GCAGTTTATC GATGAAGGCA ATTATACATC    2520

CGCCGACAAC CATACGCTGA GAGACCCTCA CTACGTTGAA GACAAAGGCC ATAAATACCT    2580

TGTATTCGAA GCCAACACGG GAACAGAAAA CGGATACCAA GGCGAAGAAT CTTTATTTAA    2640

CAAAGCGTAC TACGGCGGCG GCACGAACTT CTTCCGTAAA GAAAGCCAGA AGCTTCAGCA    2700

GAGCGCTAAA AAACGCGATG CTGAGTTAGC GAACGGCGCC CTCGGTATCA TAGAGTTAAA    2760

TAATGATTAC ACATTGAAAA AGTAATGAA GCCGCTGATC ACTTCAAACA CGGTAACTGA     2820

TGAAATCGAG CGCGCGAATG TTTTCAAAAT GAACGGCAAA TGGTACTTGT TCACTGATTC    2880

ACGCGGTTCA AAAATGACGA TCGATGGTAT TAACTCAAAC GATATTTACA TGCTTGGTTA    2940

TGTATCAAAC TCTTTAACCG GCCCTTACAA GCCGCTGAAC AAAACAGGGC TTGTGCTGCA    3000

AATGGGTCTT GATCCAAACG ATGTGACATT CACTTACTCT CACTTCGCAG TGCCGCAAGC    3060

CAAAGGCAAC AATGTGGTTA TCACAAGCTA CATGACAAAC AGAGGCTTCT TCGAGGATAA    3120

AAAGGCAACA TTTGGCCCAA GCTTCTTAAT CAACATCAAA GGCAATAAAA CATCCGTTGT    3180

CAAAAACAGC ATCCTGGAGC AAGGACAGCT GACAGTCAAC TAATAACAGC AAAAAGAAAA    3240

TGCCGATACT TCATTGGCAT TTTCTTTTAT TTCTCAACAA GATGGTGAAT TCCTGCAGCC    3300

CGGGG                                                                3305

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:2:

CCCCCAAAAA TGGATCCAAA CCGTTCGACC                                      30

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
```

-continued (D) TOPOLOGY: linear (ii) MOLECULE TYPE: DNA (genomic)

(iii) HYPOTHETICAL: NO (xi) SEQUENCE DESCRIPTION: SEQ ID NO:3:

CGATTATGGA GCGGATTGAG GATCCGGAGG                                30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:4:

AGTGGATCCC CCGGGCTGCA GGAATTCACC                                30

(2) INFORMATION FOR SEQ ID NO:5:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:5:

GAGCGCGCGA ATGTTTTCAA AATGAACGGC AAATGGTACT TGTTCACTGA TTCACTCGGT    60

TC                                                                  62